United States Patent
Lee et al.

(10) Patent No.: US 11,843,323 B2
(45) Date of Patent: Dec. 12, 2023

(54) TRANSFORMER-LESS AC-DC INPUT COMPATIBLE BOOST RESONANT INVERTER

(71) Applicant: GOODRICH CORPORATION, Charlotte, NC (US)

(72) Inventors: Yongduk Lee, Vernon, CT (US); Parag M. Kshirsagar, South Windsor, CT (US); Matthew Robert Pearson, Hartford, CT (US); Parikshith B. Channegowda, Glastonbury, CT (US)

(73) Assignee: GOODRICH CORPORATION, Charlotte, NC (US)

( * ) Notice: Subject to any disclaimer, the term of this patent is extended or adjusted under 35 U.S.C. 154(b) by 282 days.

(21) Appl. No.: 17/336,086

(22) Filed: Jun. 1, 2021

(65) Prior Publication Data
US 2022/0385205 A1  Dec. 1, 2022

(51) Int. Cl.
*H02M 7/48* (2007.01)
*A61L 2/10* (2006.01)
(Continued)

(52) U.S. Cl.
CPC ............ *H02M 7/4815* (2021.05); *A61L 2/10* (2013.01); *A61L 2/26* (2013.01); *B64D 47/02* (2013.01);
(Continued)

(58) Field of Classification Search
CPC .. H02M 5/458; H02M 7/4815; H02M 1/0058; H02M 1/083; H02M 1/10; H02M 1/4225; H02M 1/4233; H02M 5/4585; H02M 7/003; H02M 7/5387; H02M 7/53871
See application file for complete search history.

(56) References Cited

U.S. PATENT DOCUMENTS

| 6,107,756 A | 8/2000 | Parra |
|---|---|---|
| 7,009,347 B2 | 3/2006 | Henze |

(Continued)

FOREIGN PATENT DOCUMENTS

DE  102014114248  3/2016

OTHER PUBLICATIONS

European Patent Office, European Search Report dated Oct. 20, 2022 in Application No. 22171661.6.
(Continued)

*Primary Examiner* — Wei (Victor) Y Chan
(74) *Attorney, Agent, or Firm* — SNELL & WILMER L.L.P.

(57) ABSTRACT

A system for use in generating a power signal includes a first stage circuit having: a first input line coupled to a first stage first parallel line having a first stage first switch positioned thereon, a second input line coupled to a first stage second parallel line having a first stage second switch positioned thereon, and a first stage third parallel line oriented in parallel with the first stage first parallel line and the first stage second parallel line between a positive rail and a negative rail, the first stage third parallel line having a first capacitor positioned thereon. The system further includes a second stage circuit having a resonant inverter coupled between the positive rail and the negative rail and configured to output the power signal.

9 Claims, 3 Drawing Sheets

(51) Int. Cl.
*A61L 2/26* (2006.01)
*B64D 47/02* (2006.01)
*H02M 1/42* (2007.01)
*H02M 7/5387* (2007.01)
*H05B 41/36* (2006.01)
*H01J 61/12* (2006.01)

(52) U.S. Cl.
CPC ....... *H02M 1/4225* (2013.01); *H02M 7/5387* (2013.01); *H05B 41/36* (2013.01); *A61L 2202/11* (2013.01); *A61L 2202/25* (2013.01); *B64D 2203/00* (2013.01); *H01J 61/12* (2013.01)

(56) References Cited

U.S. PATENT DOCUMENTS

| | | | |
|---|---|---|---|
| 2005/0237010 | A1 | 10/2005 | Ying et al. |
| 2019/0290795 | A1* | 9/2019 | Brockschmidt .... H05B 41/3922 |
| 2020/0052608 | A1* | 2/2020 | Bala ..................... H02M 7/219 |

OTHER PUBLICATIONS

Tsorng-Juu Liang et al, "Interleaving Controlled Three-Leg Electronic Ballast for Dual-HID-Lamps", IEEE Transactions on Power Electronics, Institute of Electrical and Electronics Engineers, USA, vol. 23, No. 3, dated May 1, 2008, pp. 1401-1409.

Suja C Rajappan et al, "An efficient bridgeless power factor correction boost converter", Intelligent Systems and Control (ISCO), 2013 7th International Conference ON, IEEE, Jan. 4, 2013 (Jan. 4, 2013), pp. 55-59, DOI: 10.1109/ISCO.2013.6481122.

Darly S S et al, "A novel dual boost rectifier for power factor improvements", Electrical Energy Systems (ICEES), 2011 1st International Conference ON, IEEE, Jan. 3, 2011 (Jan. 3, 2011), pp. 122-127, DOI: 10.1109/ICEES.2011.5725314.

Mahmoud M I et al, "Design Parameters for High Frequency Series Resonance Energy Converters used as Fluorescent Lamp Electronic Ballast", Proceedings of the European Conference on Power Electronics and Applications. (EPE), AACHEN, Dusseldorf, EPE Secretariat, DE, Oct. 9, 1989 (Oct. 9, 1989), pp. 367-371, XP000143419.

* cited by examiner

TRANSFORMER-LESS AC-DC INPUT COMPATIBLE BOOST RESONANT INVERTER

FIELD

The present disclosure relates to systems and methods for providing relatively high voltage, high frequency power to an excimer bulb for use in aviation that avoids use of transformers.

BACKGROUND

Ultraviolet (UV) light has been found to be an effective disinfectant. Of the various UV wavelengths, 222 nanometers (222 nm) has been found to be particularly promising (effective and relatively safe for humans in moderate doses). Currently, UV lights that emit light of this wavelength are only available as gas-discharge excimer bulbs. These bulbs require a power signal that is of relatively high voltage and relatively high frequency. Conventional power supplies for these excimer bulbs utilize transformers (e.g., they may utilize a resonant inverter that includes transformers) which has significant limitations. These limitations may include the following: the transformer may be relatively high voltage, resulting in relatively great power losses. The power stage of the power supply may have a degrading efficiency due to changes in electrical parameters of the excimer bulb over its life. The excimer bulb may lack ignition in certain situations due to voltage variations with fixed low direct current (DC) voltages. These power supplies also utilize multiple power converting stages, which results in further loss and reduced power density.

Thus, there is a need in the art for a transformer-less analog current (AC) and DC input compatible boost resonant inverters for providing a power signal to an excimer bulb.

SUMMARY

Disclosed herein is a system for use in generating a power signal. The system includes a first stage circuit having: a first input line coupled to a first stage first parallel line having a first stage first switch positioned thereon, a second input line coupled to a first stage second parallel line having a first stage second switch positioned thereon, and a first stage third parallel line oriented in parallel with the first stage first parallel line and the first stage second parallel line between a positive rail and a negative rail, the first stage third parallel line having a first capacitor positioned thereon. The system further includes a second stage circuit having a resonant inverter coupled between the positive rail and the negative rail and configured to output the power signal.

Any of the foregoing embodiments may further include a first diode coupled between the first input line and the positive rail; and a second diode coupled between the second input line and the positive rail, wherein: the first stage first switch is coupled between the first input line and the negative rail, and the first stage second switch is coupled between the second input line and the negative rail.

In any of the foregoing embodiments, the first diode has a first anode coupled to the first input line and a first cathode coupled to the positive rail; and the second diode has a second anode coupled to the second input line and a second cathode coupled to the positive rail.

In any of the foregoing embodiments, the first stage first switch and the first stage second switch each include a transistor.

Any of the foregoing embodiments may further include a first inductor positioned on the first input line.

In any of the foregoing embodiments, the resonant inverter includes a full bridge circuit.

In any of the foregoing embodiments, the full bridge circuit includes: a second stage first parallel line coupled between the positive rail and the negative rail; a second stage second parallel line coupled between the positive rail and the negative rail; a first output line coupled to the second stage first parallel line; and a second output line coupled to the second stage second parallel line.

In any of the foregoing embodiments, the full bridge circuit further includes: a first line first switch coupled between the first output line and the positive rail; a first line second switch coupled between the first output line and the negative rail; a second line first switch coupled between the second output line and the positive rail; and a second line second switch coupled between the second output line and the negative rail.

Any of the foregoing embodiments may further include a second inductor positioned on the first output line; and a second capacitor positioned on the second output line.

In any of the foregoing embodiments, the system operates as a power supply for an excimer bulb.

In any of the foregoing embodiments, the system provides the power signal for the excimer bulb and lacks a transformer.

Also disclosed is a system for use in generating a power signal for powering an excimer bulb. The system includes a first input line coupled to a first stage first parallel line. The system further includes a second input line coupled to a first stage second parallel line, the first stage first parallel line and the first stage second parallel line coupled in parallel between a positive rail and a negative rail. The system further includes a first stage first switch positioned on the first stage first parallel line and coupled between the first input line and the negative rail. The system further includes a first stage second switch positioned on the first stage second parallel line and coupled between the second input line and the negative rail. The system further includes a second stage circuit having a full bridge circuit coupled between the positive rail and the negative rail and configured to output the power signal.

Any of the foregoing embodiments may further include a first inductor positioned on the first input line; a first stage third parallel line coupled between the positive rail and the negative rail; and a first capacitor positioned on the first stage third parallel line.

Any of the foregoing embodiments may further include a first diode coupled between the first input line and the positive rail; and a second diode coupled between the second input line and the positive rail.

In any of the foregoing embodiments, the full bridge circuit includes: a second stage first parallel line coupled between the positive rail and the negative rail; a second stage second parallel line coupled between the positive rail and the negative rail; a first output line coupled to the second stage first parallel line; and a second output line coupled to the second stage second parallel line.

In any of the foregoing embodiments, the full bridge circuit further includes: a first line first switch coupled between the first output line and the positive rail; a first line second switch coupled between the first output line and the negative rail; a second line first switch coupled between the second output line and the positive rail; and a second line second switch coupled between the second output line and the negative rail.

Any of the foregoing embodiments may further include a second inductor positioned on the first output line; and a second capacitor positioned on the second output line.

Also disclosed is a system for use in generating a power signal for powering an excimer bulb. The system includes a first input line coupled to a first stage first parallel line. The system further includes a second input line coupled to a first stage second parallel line, the first stage first parallel line and the first stage second parallel line coupled in parallel between a positive rail and a negative rail. The system further includes a first stage third parallel line coupled between the positive rail and the negative rail. The system further includes a first capacitor positioned on the first stage third parallel line. The system further includes a first inductor positioned on the first input line. The system further includes a first stage first switch positioned on the first stage first parallel line and coupled between the first input line and the negative rail. The system further includes a first stage second switch positioned on the first stage second parallel line and coupled between the second input line and the negative rail. The system further includes a second stage circuit having a full bridge circuit coupled between the positive rail and the negative rail and configured to output the power signal. The system further includes a first output line having a second inductor positioned thereon. The system further includes a second output line having a second capacitor positioned thereon.

In any of the foregoing embodiments, the full bridge circuit includes: a second stage first parallel line coupled between the positive rail and the negative rail; and a second stage second parallel line coupled between the positive rail and the negative rail; wherein: the first output line is coupled to the second stage first parallel line and the second output line is coupled to the second stage second parallel line.

In any of the foregoing embodiments, the full bridge circuit further includes: a first line first switch coupled between the first output line and the positive rail; a first line second switch coupled between the first output line and the negative rail; a second line first switch coupled between the second output line and the positive rail; and a second line second switch coupled between the second output line and the negative rail.

The foregoing features and elements may be combined in various combinations without exclusivity, unless expressly indicated otherwise. These features and elements as well as the operation thereof will become more apparent in light of the following description and the accompanying drawings. It should be understood, however, the following description and drawings are intended to be exemplary in nature and non-limiting.

BRIEF DESCRIPTION OF THE DRAWINGS

The subject matter of the present disclosure is particularly pointed out and distinctly claimed in the concluding portion of the specification. A more complete understanding of the present disclosure, however, may best be obtained by referring to the detailed description and claims when considered in connection with the figures, wherein like numerals denote like elements.

DETAILED DESCRIPTION

The detailed description of exemplary embodiments herein makes reference to the accompanying drawings, which show exemplary embodiments by way of illustration. While these exemplary embodiments are described in sufficient detail to enable those skilled in the art to practice the exemplary embodiments of the disclosure, it should be understood that other embodiments may be realized and that logical changes and adaptations in design and construction may be made in accordance with this disclosure and the teachings herein. Thus, the detailed description herein is presented for purposes of illustration only and not limitation. The steps recited in any of the method or process descriptions may be executed in any order and are not necessarily limited to the order presented.

Furthermore, any reference to singular includes plural embodiments, and any reference to more than one component or step may include a singular embodiment or step. Also, any reference to attached, fixed, connected or the like may include permanent, removable, temporary, partial, full and/or any other possible attachment option. Additionally, any reference to without contact (or similar phrases) may also include reduced contact or minimal contact. Surface shading lines may be used throughout the figures to denote different parts but not necessarily to denote the same or different materials.

The present disclosure is directed to a new power supply for supplying power to an excimer lamp in aviation applications. The power supply is based on a transformer-less and analog current (AC) and direct current (DC) input compatible design. A first stage is based on a bridge-less topology that can receive a universal AC or DC input signal, may receive a relatively wide range of input signals, may provide a variable DC voltage, and may provide power factor correction with a relatively high frequency input. A second stage has a relatively high voltage full bridge based series resonant inverter that produces a relatively high voltage high frequency output signal.

Figure 1:
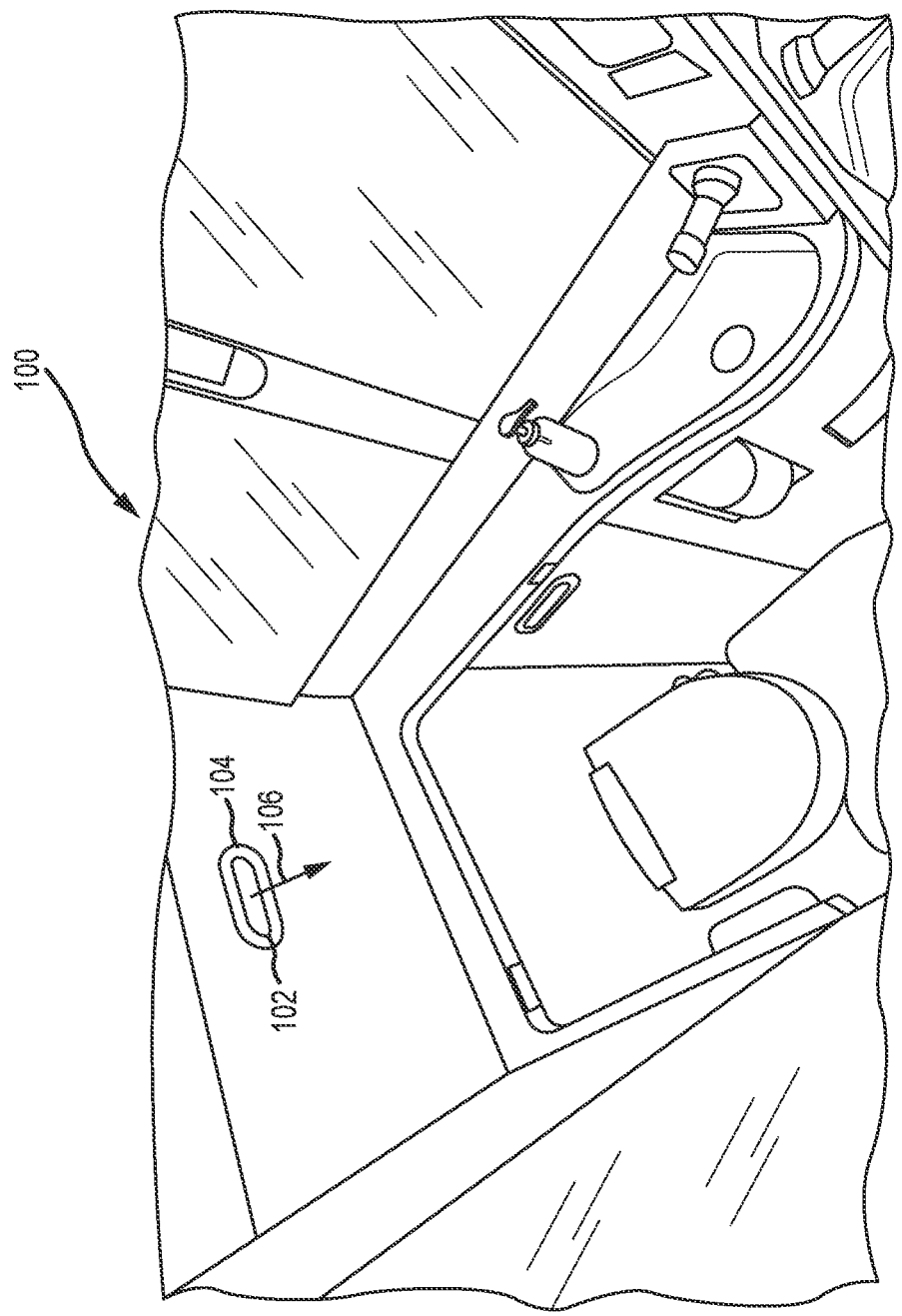
FIG. 1 illustrates an aircraft lavatory having an excimer ultraviolet bulb and a power supply for providing a power signal to the excimer bulb, in accordance with various embodiments.
Figure 2:
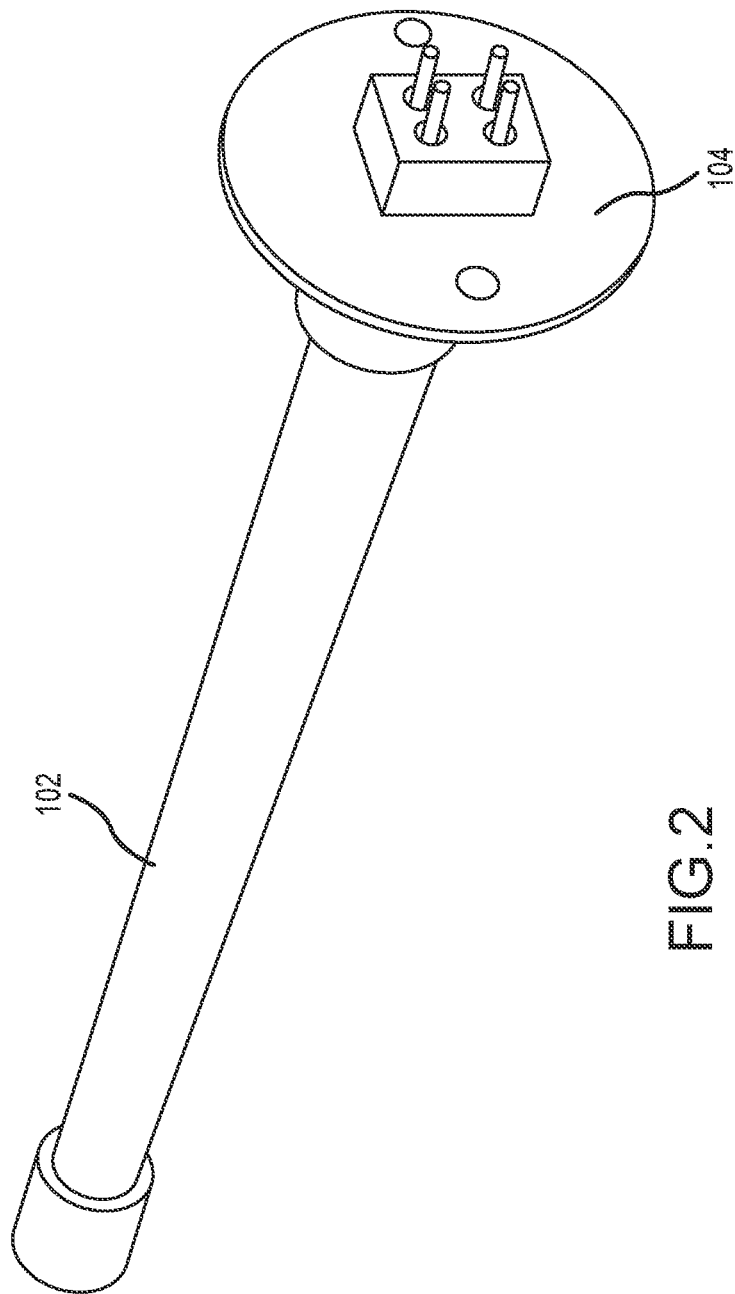
FIG. 2 is an enlarged view of the excimer bulb and the power supply of FIG. 1, in accordance with various embodiments.

Referring now to FIGS. 1 and 2, a portion of an aircraft lavatory 100 may include one or more UV excimer bulb 102. The excimer bulb 102 may emit UV light towards a portion of the lavatory 100, as shown by an arrow 106. The lavatory 100 may further include a power supply 104 designed to provide a power signal to the excimer bulb 102. In particular, the power supply 104 may provide a relatively high voltage power signal (i.e., between 500 volts and 3 kilovolts (3 kV), between 1 kV and 3 kV, or between 1.5 kV and 2.5 kV). The power supply 104 may be designed to receive either direct current (DC) input power or alternating current (AC) input power, and may output an AC output power signal. The power supply 104 may be designed to provide a desirable power signal to the excimer bulb 102 regardless of a status of the excimer bulb 102. That is, over time, the excimer bulb 102 may degrade and may have changing electrical properties as a result (e.g., a resistance or capacitance of the excimer bulb 102 may change over time). The power supply 104 is designed to compensate for these changing electrical properties of the excimer bulb 102.

Figure 3:
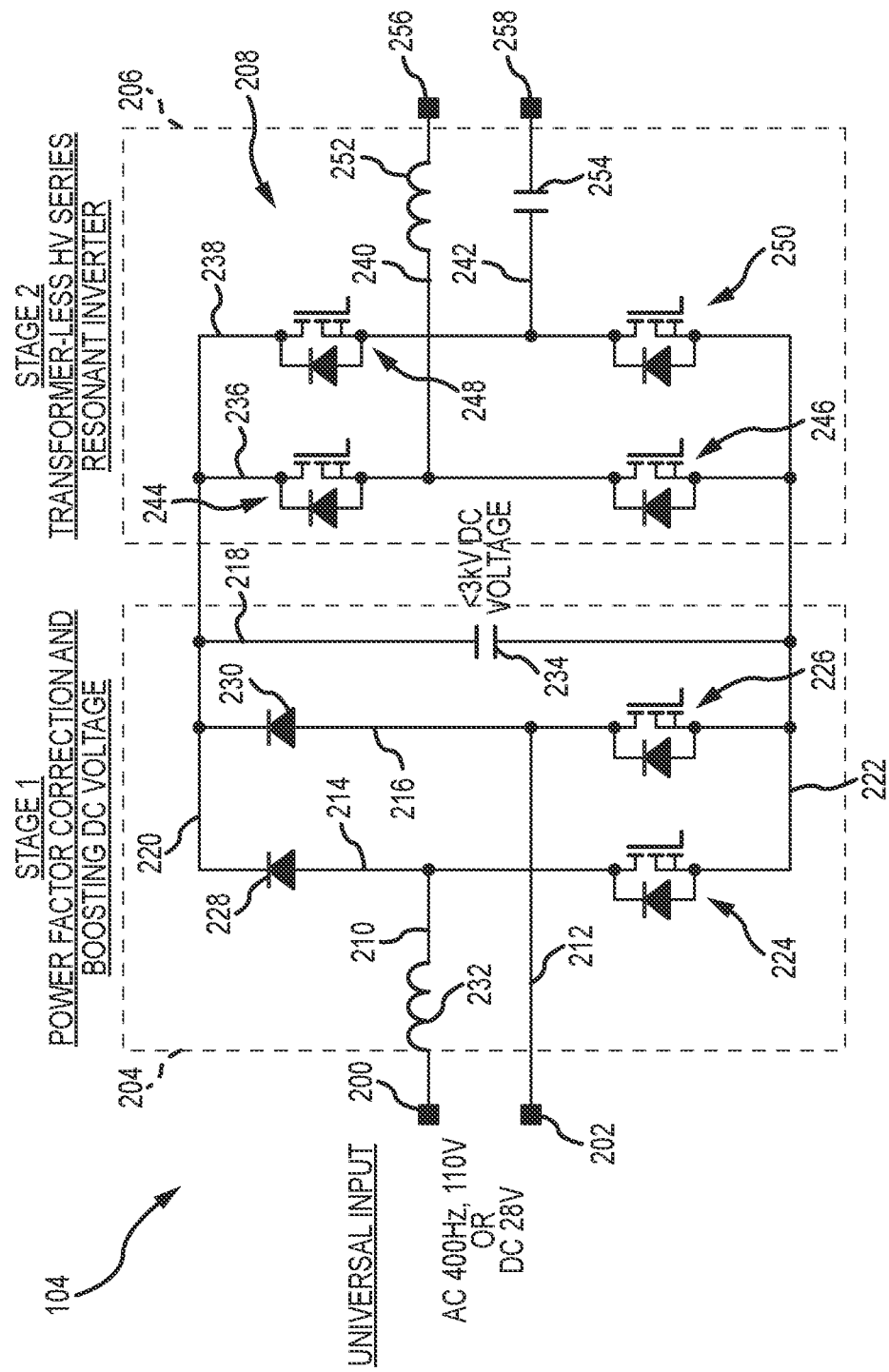
FIG. 3 is a schematic drawing illustrating features of the power supply of FIG. 1, in accordance with various embodiments.

Referring now to FIG. 3, additional details of the power supply 104 are shown. In particular, the power supply 104 may include a first input 200 and a second input 202. The first input 200 and the second input 202 may be designed to receive a DC input signal, an AC input signal, or a combined DC and AC input signal.

The power supply 104 may include a first stage 204, a second stage 206, and a resonant matching network 207. The first stage 204 may be referred to as a boosting stage and may apply power factor correction and power boosting to the input signal. The specific design of the first stage 204 is designed to handle both DC input signals and AC input signals. The first stage 204 is also designed to handle a wide range of input signals. The first stage 204 is also designed to provide a variable DC boosted voltage, and to provide a power factor correction to an input signal having a relatively high frequency (e.g., it may provide power factor correction to input signals having frequencies between 100 hertz (100 Hz) and 1.5 kilohertz (1.5 kHz), between 200 Hz and 1 kHz, or between 400 Hz and 900 Hz.

The second stage 206 may be designed to function as a resonant inverter. In that regard, the resonant inverter may include a full bridge circuit 208. The full bridge circuit 208 may include multiple switches (as described below) that may be independently controlled to cause the output power signal to have a desirable waveform.

Notably, the second stage 206 (and the first stage 204) may perform their functions without use of a transformer. This provides several benefits such as allowing the power supply 104 to function with a relatively large range of power input and output signals. In particular, power semiconductors used in the power supply may handle relatively high current power signals, which transformers are incapable of handling. Additional benefits of the power supply 104 include the ability to handle both AC input signals and DC input signals. In particular, the power supply 104 may handle input signals ranging from, for example, 28 V of DC power to 110 V of AC power. The power supply 104 may also provide the benefit of being compatible with AC input signals having relatively high frequencies (e.g., between 400 Hz and 900 Hz), allowing the power supply 104 to function as a wide bandgap device. The power supply 104 is also capable of providing relatively high efficiency with respect to variable DC voltages (i.e., relatively low loss across the range of input DC voltages), and relatively high efficiency due to the lack of transformer and a reduced quantity of power stages relative to other power supplies.

The first stage 204 may include a first input line 210 coupled to the first input 200, and a second input line 212 coupled to the second input 202. The first stage 204 may also include a first stage first parallel line 214, a first stage second parallel line 216, and a first stage third parallel line 218. The first stage first parallel line 214, the first stage second parallel line 216, and the first stage third parallel line 218 may each be coupled in parallel between a positive rail 220 and a negative rail 222.

A first stage first switch 224 may be positioned on the first stage first parallel line 214 between the first input line 210 and the negative rail 222, and a first stage second switch 226 may be positioned on the first stage second parallel line 216 between the second input line 212 and the negative rail 222. The first stage first switch 224 and the first stage second switch 226 may each include a power transistor, such as a metal-oxide-semiconductor field-effect transistor (MOSFET), a diode, or the like. A controller (not shown) may control operation of the switches 224, 226 to provide desirable signal properties on the positive rail 220 and the negative rail 222.

The first stage 204 may further include a first switch 228 positioned in the first stage first parallel line 214 and coupled between the first input line 210 and the positive rail 220, and a second switch 230 positioned on the first stage second parallel line 216 and coupled between the second input line 212 and the positive rail 220. The switches 228, 230 may include diodes. The diodes 228, 230 may have cathodes coupled to the positive rail 220, and anodes coupled to the first input line 210 and the second input line 212, respectively.

The first stage 204 may also include a first inductor 232 positioned on the first input line 210 and coupled between the first input 200 and the first stage first parallel line 214. The first stage 204 may also include a third inductor 233 positioned on the second input line 212 and coupled between the second input 202 and the first stage second parallel line 216. The first stage 204 may further include a first capacitor 234 positioned on the first stage third parallel line 218 and coupled between the positive rail 220 and the negative rail 222.

The second stage 206, as referenced above, may include the full bridge circuit 208 coupled between the positive rail 220 and the negative rail 222. That is, a first signal may be received at the second stage 206 on the positive rail 220, and a second signal may be received at the second stage 206 on the negative rail 222.

The full bridge circuit 208 may include a second stage first parallel line 236 and a second stage second parallel line 238 each coupled in parallel between the positive rail 220 and the negative rail 222. A first output line 240 may be coupled to the second stage first parallel line 236 and may provide a first output signal to a first output terminal 256, and a second output line 242 may be coupled to the second stage second parallel line 238 and may provide a second output signal to a second output terminal 258.

The full bridge circuit 208 may further include a first line first switch 244 positioned on the second stage first parallel line 236 and coupled between the positive rail 220 and the first output line 240. The full bridge circuit 208 may further include a first line second switch 246 positioned on the second stage first parallel line 236 and coupled between the first output line 240 and the negative rail 222. The full bridge circuit 208 may also include a second line first switch 248 positioned on the second stage second parallel line 238 and coupled between the positive rail 220 and the second output line 242. The full bridge circuit 208 may further include a second line second switch 250 positioned on the second stage second parallel line 238 and coupled between the second output line 242 and the negative rail 222. The full bridge circuit 208 may further include a second inductor 252 positioned on the first output line 240 such that a first end of the second inductor 252 is coupled between the first line first switch 244 and the first line second switch 246 and a second end of the second inductor 252 is coupled to the first output line 240. The full bridge circuit 208 may further include a second capacitor 254 positioned on the second output line 242 such that a first end of the second capacitor 254 is coupled between the second line first switch 248 and the second line second switch 250 and a second end of the second capacitor 254 is coupled to the second output line 242.

The resonant matching network 207 may include various combinations of inductors and capacitors. The resonant matching network 207 may be a second order (LC), a third order (LCL), or other cascaded combination of capacitors, inductors, and resistors to minimize the size and match the impedance characteristics of the UC lamp.

Benefits and other advantages have been described herein with regard to specific embodiments. Furthermore, the connecting lines shown in the various figures contained herein are intended to represent exemplary functional relationships and/or physical couplings between the various elements. It should be noted that many alternative or additional functional relationships or physical connections may be present in a practical system. However, the benefits, advantages, and any elements that may cause any benefit or advantage to occur or become more pronounced are not to be construed as critical, required, or essential features or elements of the disclosure. The scope of the disclosure is accordingly to be limited by nothing other than the appended claims, in which reference to an element in the singular is not intended to mean "one and only one" unless explicitly so stated, but rather "one or more." Moreover, where a phrase similar to "at least one of A, B, or C" is used in the claims, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C.

Systems, methods and apparatus are provided herein. In the detailed description herein, references to "various embodiments", "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

Furthermore, no element, component, or method step in the present disclosure is intended to be dedicated to the public regardless of whether the element, component, or method step is explicitly recited in the claims. No claim element herein is to be construed under the provisions of 35 U.S.C. 12(f), unless the element is expressly recited using the phrase "means for." As used herein, the terms "comprises", "comprising", or any other variation thereof, are intended to cover a non-exclusive inclusion, such that a process, method, article, or apparatus that comprises a list of elements does not include only those elements but may include other elements not expressly listed or inherent to such process, method, article, or apparatus.

What is claimed is:

1. A system for use in generating a power signal, the system comprising:
    a first stage circuit having:
        a first input line coupled between a universal input, configured to accept at least one of an alternating current (AC) or direct current (DC), and a first stage first parallel line having a first stage first switch positioned thereon, wherein the first stage first switch includes a first transistor,
        a second input line coupled between the universal input, and a first stage second parallel line having a first stage second switch positioned thereon, wherein the first stage second switch includes a second transistor, and
        the first stage first parallel line and the first stage second parallel line coupled between a positive rail and a negative rail; and
    a second stage circuit having;
        a resonant inverter coupled between the positive rail and the negative rail, configured to output the power signal, and further comprising;
            a second stage first parallel line coupled between the positive rail and the negative rail,
            a second stage second parallel line coupled between the positive rail and the negative rail,
            a first output line coupled to the second stage first parallel line,
            a second output line coupled to the second stage second parallel line,
            a first line first switch coupled between the first output line and the positive rail,
            a first line second switch coupled between the first output line and the negative rail,
            a second line first switch coupled between the second output line and the positive rail,
            a second line second switch coupled between the second output line and the negative rail,
            a second inductor positioned on the first output line such that a first end of the second inductor is coupled between the first line first switch and the first line second switch and a second end of the second inductor is coupled to the first output line, and
            a second capacitor positioned on the second output line such that a first end of the second capacitor is coupled between the second line first switch and the second line second switch and a second end of the second capacitor is coupled to the second output line.

2. The system of claim 1, further comprising:
    a first diode coupled between the first input line and the positive rail; and
    a second diode coupled between the second input line and the positive rail,
    wherein:
        the first stage first switch is coupled between the first input line and the negative rail, and
        the first stage second switch is coupled between the second input line and the negative rail.

3. The system of claim 2, wherein:
    the first diode has a first anode coupled to the first input line and a first cathode coupled to the positive rail; and
    the second diode has a second anode coupled to the second input line and a second cathode coupled to the positive rail.

4. The system of claim 3, further comprising a first inductor positioned on the first input line.

5. The system of claim 4, wherein the resonant inverter includes a full bridge circuit.

6. The system of claim 1, wherein the system operates as a power supply for an excimer bulb.

7. The system of claim 6, wherein the system provides the power signal for the excimer bulb and lacks a transformer.

8. The system of claim 1, further comprising:
    a first stage third parallel line coupled between the positive rail and the negative rail, and a first capacitor positioned on the first stage third parallel line.

9. The system of claim 1, further comprising a third inductor positioned on the second input line.

* * * * *